United States Patent [19]

McKinnie et al.

[11] 4,455,387

[45] Jun. 19, 1984

[54] MIXED DIALKYLMAGNESIUM

[75] Inventors: Bonnie G. McKinnie; Gene C. Robinson, both of Baton Rouge, La.

[73] Assignee: Ethyl Corporation, Richmond, Va.

[21] Appl. No.: 423,957

[22] Filed: Sep. 27, 1982

[51] Int. Cl.$^3$ .......................... B01J 31/12; C08F 4/50
[52] U.S. Cl. .................................. 502/153; 502/152; 260/665 R
[58] Field of Search ............... 252/431 R; 260/665 R; 502/152, 153

[56] References Cited

U.S. PATENT DOCUMENTS

| | | | |
|---|---|---|---|
| 3,597,487 | 8/1971 | Shepherd | 252/431 R X |
| 3,737,393 | 6/1973 | deVries | 252/431 R |
| 4,069,267 | 1/1978 | Kamienski et al. | 252/431 R X |
| 4,127,507 | 11/1978 | Fannin et al. | 252/431 R |
| 4,133,824 | 1/1979 | Malpass et al. | 252/431 R X |
| 4,207,207 | 6/1980 | Sanchez et al. | 252/431 R |
| 4,222,969 | 9/1980 | Fannin et al. | 252/431 R X |

*Primary Examiner*—Patrick Garvin
*Attorney, Agent, or Firm*—Donald L. Johnson; John F. Sieberth; Paul H. Leonard

[57] ABSTRACT

A process for making mixed dialkylmagnesiums wherein magnesium metal is reacted with ethylene and an alkyl halide in the presence of a hydrocarbon solvent and in a substantially moisture-free and ether-free atmosphere, under relatively high pressure and at a relatively high temperature followed by separation of undissolved solids from the resulting solution. A composition of matter produced by the process comprising dialkylmagnesium compounds having at least four different alkyl groups, a hydrocarbon solvent and a small amount of an alkyl or alkoxy aluminum compound.

31 Claims, No Drawings

MIXED DIALKYLMAGNESIUM

BACKGROUND OF THE INVENTION

Diorganomagnesium compounds are well known for their usefulness in a wide variety of chemical reactions. As reagents, these compounds can be used for the alkylation of ketones and the alkylation of metal halides or oxides to the corresponding metal alkyls. As catalysts, diorganomagnesium compounds are useful in the dimerization and polymerization of olefins, (British Pat. No. 1,251,177), the polymerization of epoxides, (U.S. Pat. No. 3,444,102), and the preparation of telomers, (U.S. Pat. No. 3,742,077). While they perform many of the same types of functions performed by Grignard reagents, diorganomagnesium compounds, owing to differences in electronic and steric factors, are more reactive than Grignard reagents toward certain types of compounds. In general, see also U.S. Pat. Nos. 3,646,231 and 3,822,219.

The utility of diorganomagnesium compounds is lessened by the fact that many are either solids or highly viscous liquids. This problem is generally overcome either by dissolving the compound in an inert hydrocarbon solvent or by solvating the compound. All are unstable upon exposure to moisture and air and require handling under an inert atmosphere. Some diorganomagnesium compounds, with straight chain lower alkyl groups of up to four carbon atoms, have a relatively low solubility by themselves in hydrocarbon solvents and thus require solubilizing agents which will form a soluble complex to achieve useful concentrations. Examples of such solubilizing agents are alkyllithium compounds (U.S. Pat. No. 3,742,077), dialkyl zinc compounds (U.S. Pat. No. 3,444,102), alkali metal hydrides (U.S. Pat. No. 3,655,790), and organoaluminum compounds (U.S. Pat. Nos. 3,143,577, 3,737,393 and 3,028,319). Certain combinations of dialkylmagnesium compounds are quite soluble in hydrocarbon solvents. The latter are seen in the *Journal of Organometallic Chemistry*, 8, 542 (1967) (methyl isobutylmagnesium) and in U.S. Pat. Nos. 4,069,267 ($C_1$ to $C_4$ di-n-alkylmagnesium and $C_6$ to $C_{18}$ dialkylmagnesium), 4,127,507 (di-n-butylmagnesium and di-ethylmagnesium), 4,207,207 (dimethylmagnesium and di-n-propylmagnesium) and 4,222,969 (dimethylmagnesium and di-nbutyl magnesium). All of these processes are relatively expensive.

Solvation involves the use of an ether or other organic Lewis base molecule to associate directly with the magnesium atom, thus yielding a hydrocarbon soluble complex. The solvated form is undesirable however, since solvation seriously inhibits the effectiveness of the compound, for some uses, particularly when the compound is used as a component of a Ziegler-type polyethylene catalyst. The use of diethylether is particularly undesirable because it has a low boiling point, is flammable, and its vapors are explosive when mixed with air. It introduces soluble RMgX according to the Schlenk equilibrium.

Even $R_2Mg$ often gives hydrocarbon solutions of relatively high viscosity which are difficult to handle and transfer. The use of chloroaryl solvents to form low viscosity solutions of the otherwise insoluble compounds, as described in U.S. Pat. No. 3,264,360 only partially solves this problem.

In addition, the relatively low solubility of the lower alkyl magnesium compounds makes preparation of them in a form free of undesirable co-product magnesium halides difficult. See in particular the direct reaction of magnesium metal with an organic halide as is disclosed in Glaze and Selman, *Journal of Organometallic Chemistry*, Vol. 5. p. 477 (1967), and W. N. Smith, *Journal of Organometallic Chemistry*, Vol. 64, p. 25 (1974). These articles deal with the preparation of diorganomagnesium compounds with straight chain alkyl groups of five carbon atoms and higher. Such compounds are soluble in hydrocarbon solvents and thus readily separable from the concurrently produced magnesium halide and unreacted magnesium. When lower straight chain alkyls are used in this process, the desired diorganomagnesium compound is formed but is largely insoluble and exists as a slurry in the solvent together with the magnesium halide and unreacted magnesium metal. Thus a solubilizing agent is required when this process is used to make lower alkyl diorganomagnesium compounds. The latter are particularly desirable as reagents and catalysts owing to their relatively low cost and high magnesium content on a weight basis.

Other methods of preparation include the mercury-magnesium exchange method, as disclosed in Cowan and Mosher, *Journal of Organic Chemistry*, Vol. 27, p. 1 (1962), and the dioxanate-precipitation method, as disclosed in Schlenk, *Berichte der Deutschen Chemischen Gaesellschaft*, Vol. 64, p. 734 (1931). The mercury method where R is alkyl, is limited by the high cost of dialkylmercury compounds and the health hazards involved in their use. The reaction itself is hazardous since it proceeds rapidly and exothermically after an inhibition period.

The dioxanate-precipitation method involves removal of magnesium halide from ether solutions of Grignard reagents by precipitation of a complex which the dioxane forms with the halide. This is a tedious process and results in an etherated dialkylmagnesium complex from which the ether must be removed prior to use as a catalyst component in Ziegler-type polymerizations.

U.S. Pat. No. 3,646,231 discloses that dialkylmagnesiums can also be prepared from alkyllithiums and magnesium halides by precipitation of lithium halide.

Such a process is unsuitable for straight-chain lower alkyl diorganomagnesiums which are insoluble in hydrocarbon solvents, since separation from co-product lithium chloride will be impossible. The use of basic solvents renders separation possible but requires subsequent desolvation.

Blitzer et al U.S. Pat. No. 2,959,625 which issued on Nov. 8, 1960 describes the manufacture of alkyl magnesium compounds by reacting magnesium hydride in a reaction medium in the presence of a catalyst, with an olefin hydrocarbon such as ethylene or propylene at a temperature of about 50° to 200° C. and elevated pressure up to about 700 atmospheres. The reaction medium may be an ether having the basicity of that of di-n-butyl ether or below or an aromatic hydrocarbon such as benzene, toluene and xylene. An inert or inactive diluent liquid such as hexane or heptane may additionally be present. A mixed dialkylmagnesium product, namely ethylpropyl magnesium is disclosed.

Podall U.S. Pat. No. 2,985,692 which issued on May 23, 1961 is similar to the Blitzer et al patent, but includes a sulfur compound such as a thioether, a sulfoxide or a sulfone in the reaction medium. A mixed dialkylmagnesium product, namely ethylisopropyl magnesium is disclosed.

Sakurai et al U.S. Pat. No. 4,120,883 which issued on Oct. 17, 1978 discloses a method of making a hydrocarbon soluble organoaluminum magnesium alkoxyalkyl complex from an organomagnesium halide and an organoaluminum halide.

Malpass et al U.S. Pat. No. 4,133,824 which issued on Jan. 9, 1979 describes organomagnesium complexes, namely a complex of magnesium alkyl and an aluminum or other Group II or IIIa metal salt of a fatty acid. The aluminum is at least 10 mole percent of magnesium.

Aishima et al U.S. Pat. No. 4,146,549 which issued Mar. 27, 1979 describes another hydrocarbon-soluble organoaluminummagnesium complex and a process for polymerizing ethylene and another olefin using the complex as a catalyst.

Shepherd U.S. Pat. No. 3,641,186 discloses a process for increasing the molecular weight of a bis-alkenyl magnesium compound by reacting the compound with an olefin in an ether medium.

Shepherd U.S. Pat. No. 3,597,488 discloses a process for increasing the molecular weight of a Grignard reagent by reacting the reagent with an olefin in an ether medium.

Shepherd U.S. Pat. No. 3,670,038 discloses a process for making higher molecular weight dialkylmagnesium compounds from lower molecular weight soluble dialkylmagnesium compounds by reacting the latter with an olefin in the presence of a non-complexing reaction solvent at a pressure of at least about 200 psig and a temperature of about 50° C. to about 250° C.

U.S. Pat. No. 2,475,520 issued to Roedel on July 5, 1949 discloses a process for polymerizing ethylene with Grignard type compounds. In such a process ethylene is polymerized at a temperature between 100° and 400° C. and a pressure between 400 and 1500 atmospheres in the presence of an anhydrous inert solvent medium, such as benzene, isooctane, xylene and diethyl ether and from about 0.005 to 5 percent by weight of a catalyst comprising magnesium metal and alkyl halide capable of yielding an organometallic complex of the formula RMgX where R is an alkyl group and X is a halogen.

Cooper et al U.S. Pat. No. 3,161,689 discloses a process for making Grignard reagents comprising reacting an olefin with an alkyl magnesium halide in a Grignard solvent medium in the presence of a titanium or zirconium catalyst. Such process provides for the use of inexpensive alkyl halides which readily form Grignard reagents to be reacted with long chain or branched chain olefins to form Grignard reagents which heretofore could not easily be obtained.

Shepherd U.S. Pat. No. 3,597,487 describes a process for making mixed dialkylmagnesiums via chain growth wherein ethylene is reacted with a Grignard reagent or diorganomagnesium compound in a non-complexing medium such as a hydrocarbon solvent, at a pressure of at least about 200 psig and a temperature of about 50° to 250° C. Additionally, the patentee discloses that catalytic or small amounts of trialkylaluminum compounds may be used to assist in the chain growth. The hydrocarbyl magnesium compound is prepared by reacting an alkyl halide with magnesium in a suitable solvent. The more readily available and less expensive alkyl halides such as ethyl chloride and propyl chloride may be used to prepare the magnesium compound.

It is an important object of the present invention to provide an improved process for making dialkylmagnesium compounds from readily available and more economical chemical compounds.

Another object of the present invention is to provide a relatively simple and economical process for making mixed dialkylmagnesium compounds and still provide substantial yields.

Still another object of the present invention is to provide a method of making mixtures containing relatively longchain dialkylmagnesium compounds.

Other objects and advantages of the invention will become more readily apparent from a consideration of the description hereinafter.

SUMMARY OF THE INVENTION

The present invention relates to a process for making mixed dialkylmagnesium by reacting an alkyl halide and ethylene with magnesium in a hydrocarbon solvent and also the product produced by the process consisting of a hydrocarbon solution of mixed dialkylmagnesium compositions. A small amount of an organoaluminum compound, including alkoxy aluminum compounds may be added to the reactants or it may be added during the reaction or after the reaction is completed.

The reaction is carried out at a pressure of at least about 200 psig and a temperature of about 50° to about 250° C. sufficient to effect the reaction without causing excessive decomposition of the desired product.

DESCRIPTION OF THE PREFERRED EMBODIMENTS

In the preferred form of the present invention, ethyl chloride and ethylene are reacted with magnesium preferably in a finely divided form. The reaction is carried out in a hydrocarbon solvent such as heptane, in a suitable pressure vessel and at a pressure of about 600 psig and a temperature of about 150° C. Ethylene and ethyl chloride are co-fed into the reactor. A small amount of recycled mixed alkylmagnesium or other activating dialkylmagnesium is added to the reaction. The amount of activating magnesium compound should be sufficient to provide the necessary activation. An amount of such compound or mixture of such compounds up to about 10 percent by volume of the hydrocarbon solvent is preferable.

A preferred pressure range is about 500 to about 1000 psig. Higher pressures may be used but no particular advantage is derived therefrom. Lower pressures may also be used, but are likely to result in smaller yields.

A preferred temperature range is about 125° C. to about 160° C. Higher temperatures may be used as long as they do not result in product decomposition. Lower temperatures are less effective.

Ethyl chloride is a preferred halide, but other halides should be suitable, e.g. ethyl bromide, ethyl iodide, propyl bromide, propyl chloride, propyl iodide, and similar homologous chlorides up to about 18 or more carbon atoms in the molecule. Other examples are butyl bromide, butyl chloride, amyl chloride, hexyl chloride, phenethyl chloride, allyl chloride and allyl iodide. Mixtures of chlorides may also be used. Methyl chloride gives significantly poorer yields than ethyl chloride alone. For purposes herein an "alkyl halide" is defined as a halide having at least two carbon atoms in the alkyl group.

Magnesium powder, −100 mesh U.S. Sieve Series is preferred. Other particulated or finely divided forms of magnesium are suitable. The best results are obtained with a form of magnesium having a relatively high surface area. A powder with a particle size equal to or less than 300 microns is very suitable. Coarser grades of magnesium normally give poorer yields. The amount of magnesium employed in the reaction is preferably about 10 mole percent excess over theory in relation to the amount of alkyl halide.

A preferred hydrocarbon solvent is heptane. Hexane or any other suitable hydrocarbon solvent may be used.

The term "hydrocarbon solvent" is used herein to designate aliphatic, cycloaliphatic, and aromatic hydrocarbons. Illustrative of aliphatic solvents are n-pentane, isopentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylenes, ethylbenzene, tetralin, and alpha-methylnaphthalene. Preferred solvents are those containing 5 to 20 carbon atoms, inclusive. More preferred are those containing 6 to 15 carbon atoms, inclusive. Particularly preferred solvents are those which have boiling points between about 60° C. and about 150° C.

In carrying out the reaction of the present invention the alkyl halide is used in an amount of about 17 weight percent of the final reaction mixture. When ethyl chloride is the alkyl halide used in the reaction, a mole ratio of magnesium to ethyl chloride of about 0.8 to about 2.0 is preferred. Ethylene is used at about 600 psig and is consumed in an amount of about five weight percent of the final mixture. Magnesium is used in an amount of about 7.3 weight percent of the mixture. Excellent results are obtained when using magnesium in amount of about 10 mole percent excess over theory in relation to the alkyl halide. The hydrocarbon solvent is used in an amount of about 70 weight percent of the final mixture.

The product formed from the reaction is a mixture of largely $C_2$ to $C_8$ dialkylmagnesiums, namely ethyl butyl hexyl octyl magnesium in a hydrocarbon solvent and undissolved solid co-products. Relatively small amounts of higher carbon atom or longer chain products may also be formed. The chain lengths form a near Poisson distribution as is discussed by Weslau for aluminum alkyls in Annalen . . . 629, 198(1960). A preferred product has the following approximate mole percentages of alkyl groups:

| ethyl | 10 to 55 |
| butyl | 20 to 45 |
| hexyl | 7 to 30 |
| octyl | 1 to 20 |
| decyl | 0 to 15 |
| dodecyl | 0 to 6 |
| tetradecyl and others | balance to 100. |

A more preferred product has the following approximate mole percentages of alkyl groups:

| ethyl | 30 to 45 |
| butyl | 30 to 45 |
| hexyl | 11 to 19 |
| octyl | 3 to 9 |
| decyl | 1.5 to 6 |
| dodecyl | 0.5 to 3 |
| tetradecyl and other | balance to 100. |

The hydrocarbon solution is separated from the undissolved solids by filtration, decanting, centrifugation, or other conventional techniques.

If desired, separation of the solution from the remaining undissolved solids can be enhanced by the use of any of the variety of viscosity reducing agents known in the art. Examples of such viscosity reducing agents are organoaluminum compounds such as trialkylaluminums, dialkylaluminum halides, alkylaluminum dihalides, aluminum trihalides, dialkylaluminum hydrides and aluminum alkoxides. If an organoaluminum compound has been already added as a growth catalyst or otherwise, no additional addition is necessary. As used herein the term "organoaluminum compounds" includes alkoxides, halides and hydrides as well as aluminum alkyls.

Some specific examples of these organoaluminum compounds or viscosity reducing agents are triethylaluminum, tri-n-propylaluminum, diethylaluminum chloride, ethylaluminum dichloride, isoprenyl aluminum, diethylaluminum iodide, diisobutyl aluminum hydride, and aluminum isopropoxide.

The organoaluminum compound is preferably added in an amount of about 1.4 mole percent of the ethyl chloride charge and may be added before the reaction is begun, during the reaction or after the reaction is completed. Larger amounts up to about 10 mole percent of the ethyl chloride or alkyl halide charge may be added without harm.

Magnesium alkyls are pyrophoric substances, capable of spontaneous ignition upon contact with air. To prevent such ignition, and also to prevent oxidation of the dialkylmagnesium product, the reactions must be carried out in the absence of more than trace amounts of oxygen. Thus, the reactions are normally carried out in an atmosphere of inert gas such as nitrogen or argon. The reactions must also be conducted in the substantial absence of water, due to the susceptibility of the system components to decomposition in the presence of water.

The pressure under which the reaction is conducted critically affects the extent of chain growth. Pressures ranging from about 200 psig or up can be employed. The reaction may be run at the lowest pressure necessary to give at least about 50 percent conversion of ethyl groups to higher alkyl groups and thus keep the reactants in solution. The preferred pressure range in this case is about 200 psig to about 1000 psig. Higher pressures and longer reaction times give longer chain lengths.

GENERAL PROCEDURE

The present invention is further illustrated by the following examples.

Unless stated otherwise, reactions were carried out in a 300 ml stainless steel autoclave equipped with a Magnedrive stirrer, thermocouple well, water cooling coils, and two inlet valves. Magnesium, heptane, aluminum isopropoxide, and activating dialkylmagnesium solution were charged to the autoclave in a dry box, then the autoclave was sealed.

Ethylene was added as a gas through a high pressure regulator as needed to maintain the desired pressure.

Ethyl chloride was added from a steel cylinder, approximately one-fourth full. The cylinder was pressured to 1000 psig with nitrogen before addition was begun. The cylinder was mounted on a balance such that the rate of addition of ethyl chloride could be followed by weight loss. The rate of addition was controlled by a Whitey micro-metering valve.

Reactions carried out on a scale larger than 300 ml were performed in an identical manner except reagents were charged to the sealed autoclave by means of a diptube. The transfer of all reagents and products was carried out either in a dry nitrogen box or under a nitrogen blanket.

Magnesium was −100 mesh U.S. Sieve Series powder obtained from Reade Mfg. Co.

Ethylene was a standard commercial grade obtained from Matheson.

The alkyl halide was a standard commercial grade ethyl chloride obtained from Ethyl Corp. The hydrocarbon solvent was a pure grade heptane obtained from Phillips Petroleum Co. and was dried over 4A Molecular Sieves and degassed with a stream of nitrogen before being used.

The organoaluminum viscosity reducing compound was aluminum isopropoxide obtained from the Ventron Division of Thiokol Corp.

EXAMPLE 1

Reaction of Diethylmagnesium With Ethylene

Following the General Procedure, a 300 ml stainless steel autoclave was charged with 11.77 grams (0.484 gram-atom) of magnesium powder, 125 ml of heptane and 1.4 ml of a solution of dialkylmagnesium in heptane (4.79 weight percent Mg). After heating to 90° C., 4.6 ml. (44 mmole) of butyl chloride was added to activate the magnesium. The mixture was heated with stirring at 98° C. as 25.8 grams (0.40 mole) of ethyl chloride was added over 1.5 hours. Ethylene pressure of 300 psig was applied. The mixture was heated to 150° C., and then pressured to 800 psig of ethylene.

After heating at 150° C. under 800 psig of ethylene for four hours the autoclave was cooled, and 1.1 grams of aluminum isopropoxide in 9 ml heptane was added. After reheating at 95° C. for a few minutes the autoclave was cooled, vented, and the clear liquid portion decanted. Analysis of it showed 1.69 weight percent magnesium versus a calculated maximum of 4.35 weight percent magnesium (39% yield).

EXAMPLE 2

Reaction of Diethylmagnesium With Ethylene in the Presence of Aluminum Isopropoxide Following the General Procedure, a 300 ml autoclave was charged with 10.2 grams (0.42 grams-atom) of magnesium, 142 ml heptane, 0.95 grams aluminum isopropoxide, and 10 ml of a dialkylmagnesium solution (2.9 percent Mg). This was heated to 100° C. and 25.0 grams (0.387 mole) of ethyl chloride added slowly over three hours. It was then pressured to 800 psig with ethylene and heated at 150° C. for 3.5 hours.

The autoclave was cooled, vented, and the clear upper layer decanted. Analysis of this liquid showed 2.14 weight percent Mg; calculated 4.06 percent Mg (53% yield).

EXAMPLE 3

Reaction of Ethyl Chloride With Magnesium and Ethylene

Following the General Procedure a mixture of 11.8 grams (0.484 gram-atom) of magnesium, 165 ml heptane, 8.0 ml of a dialkylmagnesium solution (2.9 weight percent Mg), and 1.1 grams of aluminum isopropoxide was heated in a 300 ml autoclave to 140° C. and pressured to 700 psig with ethylene. Keeping pressure at 700 psig with additional ethylene, ethyl chloride, 28.3 g (0.44 mole) was added over a four hour period from a pressurized vessel. After all ethyl chloride had been added ethylene pressure was increased to 1000 psig and heating at 140° C. was continued for two hours. After cooling and venting the clear liquid was decanted and analyzed. Found 2.85; 2.79 weight percent Mg, 0.20 weight percent chloride; calculated 4.00 weight percent Mg (71% yield). Analysis of the hydrolysate gas and liquid showed the following composite mole percent of each alkyl group: ethyl, 25%; butyl, 35%; hexyl, 18%; octyl, 9%; decyl, 6%; dodecyl, 2.1%; and tetradecyl, 0.8%.

EXAMPLE 4

One-liter Reaction

Following the procedure of Example 3, in a one-liter stainless steel autoclave was placed 36.1 grams (1.48 gram-atom) of magnesium, 500 ml heptane, 3.6 grams aluminum isopropoxide, and 36 ml of a solution of dialkylmagnesium (2.8 weight percent Mg). This was pressured to 200 psig ethylene, heated to 146° C. and the ethylene pressure raised to 600 psig. Ethyl chloride (87.0 grams, 1.35 mole) was added slowly over two hours. Heating at 146° C. under 600 psig was continued one hour longer. The reactor was then cooled, vented, and the content transferred. The clear liquid obtained after all solids settled was found to contain 0.29 weight percent chloride, 0.11 weight percent aluminum, and 3.06 weight percent magnesium; calculated 4.01 weight Mg (76% yield). Analysis of the hydrolysate gas and liquid showed the following mole percent of each alkyl group: ethyl, 29%; butyl 35%; hexyl, 18.5%; octyl, 8.5%; decyl, 4.6%; dodecyl, 2.4%; and tetradecyl, 0.6%.

EXAMPLE 5

Five-Gallon Reaction

Continuing the General Procedure, a five-gallon stainless steel autoclave was charged with 754 grams (31 mole) of magnesium powder, 7180 grams commercial heptane, 340 grams of a dialkylmagnesium solution (2.5 weight percent Mg), and 75 grams aluminum isopropoxide. After heating to 150° C. under 600 psig of ethylene, 1920 grams (29.7 mole) of ethylene chloride was added over 1.5 hours. Heating at 140° C. under 600 psig of ethylene was continued 1.5 hours longer. The reactor was then cooled and vented. After settling 18 hours the clear liquid was decanted giving 7460 grams of product. Analysis showed it contained 0.26 weight percent chloride, 0.11 weight percent aluminum, and 3.10 weight percent magnesium; calculated 4.22 weight percent magnesium (73% yield).

Examples 1 and 2 represent prior art reactions. Examples 3 to 5 represent the present invention. It is clear that unexpected increases in product yield (weight percent Mg) are obtained using the co-feed process.

The present invention has the utility of diorganomagnesium compounds as set forth hereinbefore, the utility of making such compounds and the further utility of increasing the solubility of such compounds. The composition of the invention is particularly useful as a catalyst component in the polymerization of olefins.

The foregoing disclosure and description of the invention is illustrative and explanatory thereof and various changes in the illustrated process may be made within the scope of the appended claims without departing from the spirit of the invention.

What is claimed is:

1. A process for the manufacture of a hydrocarbon solution of a mixed dialkylmagnesium comprising:
   (a) reacting, in the presence of a hydrocarbon solvent, magnesium metal with ethylene and an alkyl halide, to form a mixture of a hydrocarbon solution of a mixed dialkylmagnesium composition and undissolved solids;
   (b) separating the hydrocarbon solution from the undissolved solids; and,
   (c) recovering a mixed dialkylmagnesium product.

2. The process of claim 1, wherein an organoaluminum catalyst or viscosity reducing agent is added in step (a).

3. The process of claim 2, wherein the organoaluminum catalyst or viscosity reducing agent is added in an amount of up to about 10 mole percent of the alkyl halide reactant.

4. The process of claim 2, wherein the alkyl halide reactant is ethyl chloride and the organoaluminum catalyst or viscosity reducing agent is added in an amount of about 1.4 mole percent of the ethyl chloride.

5. The process of claim 1, wherein all steps are conducted in a substantially moisture-free and oxygen free atmosphere.

6. The process of claim 1, wherein the alkyl halide is ethyl chloride.

7. The process of claim 1, wherein the hydrocarbon solvent is an aliphatic, cycloaliphatic, or aromatic hydrocarbon containing from 5 to 20 carbon atoms.

8. The process of claim 1, wherein the reaction is carried out under a pressure of at least 200 psig.

9. The process of claim 1, wherein the reaction is carried out under a pressure of about 500 to 1000 psig.

10. The process of claim 1, wherein the reaction is carried out under a pressure of about 600 to 800 psig.

11. The process of claim 1, wherein the magnesium metal is a magnesium powder and is about 10 mole percent excess over theory in relation to the amount of the alkyl halide.

12. The process of claim 1, wherein the hydrocarbon solvent is a liquid paraffin hydrocarbon having a boiling point at atmospheric pressure of about 60° C. to about 150° C.

13. The process of claim 1, wherein the hydrocarbon solvent is heptane.

14. The process of claim 1, wherein a small amount of recycled mixed alkylmagnesium up to about 10 percent by volume of the hydrocarbon solvent is added to the reaction.

15. The process of claim 1, wherein a relatively small amount of an alkyl or alkoxy aluminum compound is added before the reaction is started, during the reaction or after the reaction is completed.

16. The process of claim 15, wherein said alkyl or alkoxy aluminum compound is in an amount of up to about 10 percent mole of alkyl halide.

17. The process of claim 1, wherein ethylene and alkyl halide are simultaneously fed into the reaction.

18. The process of claim 1, wherein the amount of reactants in weight percent of the reaction mixture weight is as follows:
    alkyl halide—17
    ethylene—5
    magnesium metal—7.3

19. The process of claim 1, wherein the amount of hydrocarbon solvent used is in an amount sufficient to keep the reactants in solution.

20. The process of claim 1, wherein the alkyl halide is ethyl chloride, the magnesium metal is a magnesium powder of about 100 microns or less and the hydrocarbon solvent is a liquid paraffinic hydrocarbon having a boiling point at atmospheric pressure of about 60° C. to about 150° C. and the reaction is carried out at a pressure of from about 500 to 1000 psig and a temperature of about 125° C. to about 160° C.

21. A process for the manufacture of a hydrocarbon solution of a mixed dialkylmagnesium composition comprising:
   (a) reacting, in the presence of a hydrocarbon solvent, magnesium metal with ethylene and ethyl chloride, to form a mixture of a hyrocarbon solution of a mixed dialkylmagnesium composition and undissolved solids;
   (b) separating the hydrocarbon solution from the undissolved solids; and
   (c) recovering a mixed dialkylmagnesium composition product.

22. The process of claim 21, wherein an organoaluminum catalyst or viscosity reducing agent is added in step (a).

23. The process of claim 21, wherein all steps are conducted in a substantially moisture-free and oxygen-free atmosphere.

24. The process of claim 21, wherein the reaction is carried out at a pressure of at least about 200 psig.

25. The process of claim 21, wherein the reaction is carried out at a temperature of about 50° C. to about 250° C.

26. The process of claim 21, wherein the hydrocarbon solvent is a member selected from the group consisting of aliphatic, cycloaliphatic, and aromatic hydrocarbons containing from 5 to 20 carbon atoms.

27. The process of claim 21, wherein the mole ratio of magnesium to ethyl chloride is about 0.8 to about 2.0.

28. The process of claim 21, wherein the reaction is carried out at a temperature of from about 50° C. to about 250° C.

29. The process of claim 21, wherein the reaction is carried out at a pressure of at least 200 psig and temperature of about 50° C. up to about the decomposition temperature of the dialkylmagnesium compounds.

30. A process for the manufacture of a hydrocarbon solution of a mixed dialkylmagnesium comprising:
   (a) charging to an autclave, in a substantially moisture-free and ether-free inert atmosphere, finely divided magnesium metal, a hyrocarbon solvent, an activating dialkylmagnesium solution, and an organoaluminum viscosity reducing agent;
   (b) co-feeding ethylene and an alkyl halide under relatively high pressure into the autoclave;
   (c) heating and reacting the resulting mixture in the autoclave at a temperature sufficiently high to effect the reaction without causing decomposition of the dialkylmagnesium product and at a pressure of at least 200 p.s.i.g.;
   (d) separating the hydrocarbon solution from undissolved solids; and
   (e) recovering a mixed dialkylmagnesium product comprising at least four different alkyl groups ranging from two carbon atoms up to about 22 carbons.

31. A process for the manufacture of a hydrocarbon solution of a mixed dialkylmagnesium comprising:
(a) charging to an autoclave in a substantially moisture-free and ether-free inert atmosphere, finely divided magnesium metal, a hydrocarbon solvent, an activating dialkylmagnesium solution, and an organoaluminum viscosity reducing agent;
(b) co-feeding ethylene and ethyl chloride under relatively high pressure into the autoclave;
(c) heating and reacting the resulting mixture in the autoclave at a temperature sufficiently high to effect the reaction without causing decomposition of the dialkylmagnesium product and at a pressure of at least 200 p.s.i.g.;
(d) separating the hydrocarbon solution from undissolved solids; and,
(e) recovering a mixed dialkylmagnesium product comprising at least four different alkyl groups largely being ethyl, butyl, hexyl and octyl groups.

* * * * *